(12) United States Patent
Grayden et al.

(10) Patent No.: US 7,787,956 B2
(45) Date of Patent: Aug. 31, 2010

(54) GENERATION OF ELECTRICAL STIMULI FOR APPLICATION TO A COCHLEA

(75) Inventors: David Bruce Grayden, Heathmont (AU); Anthony Neville Burkitt, South Yarra (AU); Owen Patrick Kenny, Queensland (AU); Janine Catherine Clarey, Caulfield North (AU); Antonio Giacomo Paolini, Bulleen (AU); Graeme Milbourne Clark, Eltham (AU); Peter Francis Duke, Heathmont (AU)

(73) Assignee: The Bionic Ear Institute, East Melbourne, Victoria (AU)

( * ) Notice: Subject to any disclaimer, the term of this patent is extended or adjusted under 35 U.S.C. 154(b) by 0 days.

(21) Appl. No.: 10/996,758

(22) Filed: Nov. 24, 2004

(65) Prior Publication Data

US 2005/0192646 A1 Sep. 1, 2005

Related U.S. Application Data

(63) Continuation-in-part of application No. PCT/AU03/00639, filed on May 26, 2003.

(30) Foreign Application Priority Data

May 27, 2002 (AU) .................................... PS 2590

(51) Int. Cl.
*A61N 1/08* (2006.01)
(52) U.S. Cl. .......................................................... 607/57
(58) Field of Classification Search .............. 607/55–57, 607/136, 137; 600/379; 381/312
See application file for complete search history.

(56) References Cited

U.S. PATENT DOCUMENTS

| | | | |
|---|---|---|---|
| 4,207,441 A | 6/1980 | Ricard et al. | |
| 4,400,590 A | 8/1983 | Michelson | |
| 4,823,795 A * | 4/1989 | van den Honert | 607/56 |
| 4,905,285 A | 2/1990 | Allen et al. | |
| 5,597,380 A * | 1/1997 | McDermott et al. | 607/57 |
| 5,749,912 A | 5/1998 | Zhang et al. | |
| 6,480,820 B1 * | 11/2002 | Clopton et al. | 704/203 |

FOREIGN PATENT DOCUMENTS

| | | |
|---|---|---|
| AU | 657959 | 3/1995 |
| JP | 06214597 A | 8/1994 |

(Continued)

OTHER PUBLICATIONS

Search report dated Jun. 19, 2003 for PCT/AU03/00639.

(Continued)

*Primary Examiner*—Mark W Bockelman
*Assistant Examiner*—Eric D. Bertram
(74) *Attorney, Agent, or Firm*—Scully, Scott, Murphy & Presser, P.C.

(57) ABSTRACT

A method for processing sound signals to generate electrical stimuli for an auditory prosthesis electrode array including a plurality of electrodes, the method including: deriving (10) one or more filtered representations (FIGS. 3 and 4) of an incoming audio signal; and, generating (11) a series of spikes from each filtered signal representation to directly control electrode stimulation. Each spike has a temporal position based upon an instant at which the filtered signal representation crosses a predetermined threshold ($\bar{y}$;0).

55 Claims, 4 Drawing Sheets

FOREIGN PATENT DOCUMENTS

| | | |
|---|---|---|
| WO | WO 91/03913 | 3/1991 |
| WO | WO 01/03622 | 1/2001 |
| WO | WO 01/31632 | 5/2001 |
| WO | WO 01/99470 | 12/2001 |
| WO | WO 02/32501 | 4/2002 |

OTHER PUBLICATIONS

Donaldson et al., "Derived band auditory brain-stem response estimates of travelling wave velocity in humans. I: Normal-hearing subjects", J. Acoust. Soc. Am. 93(2):940-951 (1993).

Kim et al. "Auditory processing of speech signals for robust speech recognition in real-world noisy environments", IEEE T-SAP 7(1), 55-69 (1999).

Kitazawa et al., "Acoustic simulation of auditory model based speech processor for cochlear implant system", Proc. of the Int. Conf. on Spoken Language Processing, ICSLP'94, pp. 2043-2046 (1994).

Meyer-Bäse et al. "Auditory Neuron Models for Cochlea Implants", SPIE AeroSense, Orlando, Florida, UAS; vol. 3077, pp. 582-593 (Apr. 1997).

Meyer-Bäse, "An interspike interval method to compute speech signals from neural firing", SPIE AeroSense, Orlando, Florida, UAS; vol. 3390, pp. 560-571 (Apr. 1998).

Meyer-Bäse et al., "An inter-spike interval method for computing phase locking from neural firing", Biol. Cybern. 82, 283-290 (2000).

\* cited by examiner

GENERATION OF ELECTRICAL STIMULI FOR APPLICATION TO A COCHLEA

CROSS-REFERENCE TO RELATED APPLICATIONS

This is a continuation in part of International Application No. PCT/AU03/000639, filed on May 26, 2003. International Application No. PCT/AU03/000639 claims priority of Australian Provisional Patent Application No. PS2590, entitled "Generation of electrical stimuli for application to a cochlea," filed on May 27, 2002.

The present invention relates generally to the generation of electrical stimuli for application to a cochlea via an auditory prosthesis electrode array.

The first successful multi-channel cochlear implant was implanted in 1978. Early signal processing designs extracted the second formant (F2) and pitch (F0) to control electrode stimulation. The frequency of F2 controlled the location of electrode stimulation, and F0 controlled the rate of stimulation. Improvements were made by also extracting the first formant (F1) and adding a second stimulated electrode for each pitch period. The MULTIPEAK stimulation strategy added stimulation of a number of fixed electrodes to better represent high-frequency information. The next stages of development were the Spectral Maxima Sound Processor (SMSP) strategy, described in Australian Patent No. 657,959, and SPEAK strategy, described in U.S. Pat. No. 5,597,380. These were a departure from the others as they used a fixed stimulation rate and stimulated electrodes that corresponded to maxima in the sound spectra. Another fixed-rate strategy, CIS, is described in U.S. Pat. No. 4,207,441. This strategy stimulated all of a small number of electrodes to represent the sound spectra. All of the above processing strategies involve fixed-rate sound processing.

Kitazawa et al. (Kitazawa, S, Muramoto, K. and Ito, J. (1994) "Acoustic simulation of auditory model based speech processor for cochlear implant system", Proceedings of the International Conference on Spoken Language Processing, ICSLP'94, pp. 2043-2046) describes a strategy for the spectra/CI-22 system using an auditory model for choosing electrodes to stimulate and for extracting fundamental frequency to control rate of stimulation. This strategy was tested by simulation with normal hearing listeners. Stimulation was restricted to low rates and required explicit extraction of pitch information. Performance was reduced for word recognition compared to the Wearable Speech Processor (WSP) running MULTIPEAK.

The SMSP strategy was further expanded by an invention entitled "Emphasis of short-duration transient speech features" (PCT/AU00/01310, International Publication Number WO 01/31632 A1). Together with SMSP, this strategy is called the "Transient Emphasis Spectral Maxima Sound Processor" (TESM). This strategy used the same signal processing and electrode selection method as SMSP except that the relative amplitude of short-duration amplitude transitions was increased before electrode selection in order to assist in perception of short, low-amplitude speech sounds.

More recently the "Multi-rate cochlear stimulation strategy and apparatus" (PCT/AU00/00838, International Publication Number WO 01/03622 A1) has been developed that does not use fixed stimulation rates. The strategy determines rate of stimulation for each implant electrode by measuring average intervals between positive zero-crossings of the filtered signals for each band.

Another recent development is "Sound processor for a cochlear implant" (PCT/AU01/00723, International Publication Number WO 01/99470 A1) called the "Travelling Wave Strategy". This device models the spatio-temporal neural excitation patterns induced by basilar membrane motion in the normally hearing listener to produce electrical stimulation patterns for the cochlear implant user. The device contains a basilar membrane motion model, and inner and outer hair cell models, to provide 3-dimensional (position, time, amplitude) excitation patterns that may more closely mimic those of the normally hearing listener.

Meyer-Bäse et al. (Meyer-Bäse, U., Meyer-Bäse, A., and Scheich, H. (1997) "Auditory Neuron Models for Cochlea Implants", SPIE AeroSense, April 1997, Orlando, Fla., UAS; Vol 3077, pp. 582-593; Meyer-Bäse, U. (1998) "An interspike interval method to compute speech signals from neural firing", SPIE AeroSense, April 1998, Orlando, Fla., UAS; Vol 3390, pp. 560-571; Meyer-Bäse, U., Meyer-Bäse, A., and Scheich, H. (2000) "An inter-spike interval method for computing phase locking from neural firing", Biol. Cybern. 82, 283-290) developed a neural model with the aim of extracting inter-spike intervals for control of cochlear implant stimulation. However, this work was on the development of hardware for implementing auditory models and the papers give no details of how the cochlear implant strategy would be implemented.

It would be desirable to provide a method and system for generating electrical stimuli for application to a cochlea via an auditory prosthesis electrode array that more closely replicates cochlea stimulation of a normal hearing listener.

It would also be desirable to provide a method and system for generating electrical stimuli for application to a cochlea that ameliorates or overcomes one or more disadvantages of known electrical stimuli generation methods and systems.

One aspect of the present invention provides a method for processing sound signals to generate electrical stimuli for an auditory prosthesis electrode array including a plurality of electrodes, the method including:

deriving one or more filtered representations of an incoming audio signal; and generating a series of spikes from each filtered representation to directly control electrode stimulation, wherein each spike has a temporal position based upon an instant at which the filtered signal representation crosses a predetermined threshold.

The amplitude of each spike may be derived from the amplitude of a filtered signal representation peak following the threshold crossing. Spike amplitude may be equal to the difference between the predetermined threshold and the amplitude of a filtered signal representation peak following the threshold crossing. Alternatively, spike amplitude may equal to the amplitude of a filtered signal representation peak following the threshold crossing.

In one embodiment, each spike may have a temporal position based upon an instant at which the filtered signal representation crosses a zero axis in a positive direction. In another embodiment, each spike may have a temporal position based upon an instant at which the filtered signal representation crosses a zero axis in a negative direction.

The amplitude of each spike may be derived from the amplitude of a filtered signal representation peak following the zero axis crossing. Spike amplitude may be equal to the difference between a predetermined threshold and the amplitude of a filtered signal representation peak following the zero axis crossing. Alternatively, spike amplitude may be equal to the amplitude of a filtered signal representation peak following the zero axis crossing.

The method may further include delaying the temporal position of each spike according to a travelling wave delay for a normally hearing person along the length of the electrode array.

The method may further include adapting the threshold based on long term average energy of the filtered signal representation.

The method may further include computing a neural adaptation variable from an integral of previous spikes in the spike series and from a decay function; and applying a gain derived from the neural adaptation variable to the amplitude of each spike.

The method may further include limiting the number of spikes used to generate the electrical stimuli for each electrode so that the number of times a particular electrode is stimulated within a stimulation sequence window does not exceed a fixed maximum average rate.

The method may further include sorting spikes occurring within a stimulation sequence window in order of importance; and selecting a number of the sorted spikes in order of importance to derive an electrode stimulation sequence for generating electrical stimuli. The spike importance may be determined by normalised amplitude.

The method may further include configuring normalisation coefficients for comparison and prioritisation of spikes in different frequency regions.

The method may further include obtaining the electrode stimulation sequence by progressively placing spikes occurring within the stimulation sequence window in stimulation time slots corresponding to the temporal positions of the spikes in decreasing order of importance from a sorted list of normalised amplitude spikes.

The method may further include mapping electrical stimuli to a current level for a particular user using a loudness growth function and stored threshold and comfort levels for that particular user, wherein the mapping uses a special comfort level for short duration transition events to provide increased stimulation levels during neural response adaptation.

The method may further include encoding the electrode stimulation sequence; and transmitting the encoded electrode stimulation sequence to the auditory prosthesis electrode array to enable stimulation of an auditory nerve or cochlea nucleus.

Another aspect of the invention provides a system for stimulating an auditory prosthesis electrode array, including:

a stimulator unit for selectively stimulating electrodes in the electrode array; and a processor for processing received sound signals and control of the operation of the stimulator unit by carrying out a method as previously described.

Yet another aspect of the invention provides a processor for use in a system for stimulating an auditory prosthesis electrode array, including a stimulator unit for selectively stimulating electrodes in the electrode array, the processor including digital signal processing means for processing received sound signals and controlling the operation of the stimulator unit by carrying out a method as previously described.

In essence, the strategy implemented by the present invention simulates the behaviour of the hair cells of the cochlea and of the auditory nerve to create a spike-based representation modelled on action potentials generated in the auditory neurons. The cochlea is electrically stimulated using a sequence of electrical pulses that replicates this spike-based representation as closely as possible within device limitations.

The Spike-based Temporal Auditory Representation (STAR) strategy of the present invention improves speech perception ability in the presence of noise, including both pseudo-stationary random noise and multi-talker babble. This is achieved by providing an improved representation of fine-grained temporal information, especially phase locking to formants across multiple stimulation channels. Adaptation effects improve detection of transient events, such as plosive onsets and formant transitions, and help to overcome pseudo-stationary background noise by a neural adaptation process similar to spectral subtraction.

The incoming acoustic signal may be passed through a filter bank in which the centre-frequencies are distributed according to an auditory/psychophysics-based distribution of frequencies. The filters may have significant overlap based on equivalent rectangular bandwidth. Either linear or non-linear filters may be used.

A series of "spikes" are extracted from each filtered representation of the signal, each spike having a temporal position or "spike time" based upon the instance at which the signal crosses a threshold in a positive-going direction. The amplitude of the spike may be determined by the difference between the threshold and the following maximum of the signal. In certain embodiments the "spike time" of each spike can be based upon the instance at which the signal crosses a threshold in a negative-going direction. In this case, the amplitude of the spike may be determined by the difference between the threshold and the following minimum of the signal.

Neural adaptation effects may be incorporated to emphasise onsets of signals relative to the steady-state amplitudes as is observed in physiological studies. A time-dependent integral may be computed from the series of spikes in each channel (the value of this integral decays in time if there are no subsequent spikes), and a gain applied to the amplitude of each spike by a measure related to this sum.

The value of the threshold may be adjusted based on signal history (i.e. threshold adaptation), in order to take account of differing listening conditions and levels of background noise. The amplitudes of the spikes may also be adjusted based on the recent signal history, in order to model neural adaptation effects and allow increased responses at the onset of acoustical stimuli.

Electrodes may be stimulated at threshold crossing times (delayed across all electrodes by up to 10 msec to allow peak detection) using stimulus levels proportional to the adapted amplitudes. Owing to limitations in existing cochlear implants, a limited number of electrodes may be chosen for stimulation by selecting channels with the highest normalised average amplitude. Temporal contention (i.e. simultaneous spikes) may be accounted for by systematically shifting spikes to other times based on their importance, which are determined using normalised amplitudes. Average rate of stimulation may be limited on each electrode by ensuring that spikes in high frequency channels are not stimulated above a fixed maximum average rate.

The present invention builds upon a rich history of auditory modelling. One of the most prominent such models is that developed by Allen & Ghitza (U.S. Pat. No. 4,905,285) in the context of developing improved strategies for automatic speech recognition based upon the human auditory system. A similar system was developed by Kim et al. (Kim, D-S, Lee, S-Y and Rhee, M (1999) "Auditory processing of speech signals for robust speech recognition in real-world noisy environments", IEEE T-SAP 7(1), 55-69) that used a single zero-crossing measure to locate spikes and determined their amplitudes using the subsequent peak of the filtered signal.

The present invention uses a similar auditory model to Kitazawa et al. (1994) for the pre-processing of the incoming waveform, but uses a spike-train directly to control the electrode simulation rather than extract F0 explicitly to control rate of stimulation across the electrode array. Explicit extraction of pitch is not required to control the overall rate of stimulation but may be represented by the stimulation sequence of the more apical electrodes and by the amplitude modulation over the whole electrode array. Direct extraction of spike trains with fine-grained temporal information also distinguishes this invention from the Multi-rate strategy.

The Travelling Wave Strategy is similar to the STAR strategy of the present invention in that it extracts precise timing information that is useful for higher levels of processing in the cochlear nucleus and other stages of the brainstem. However, the Travelling Wave Strategy relies on specific basilar membrane properties that are not used in STAR, while STAR relies more on auditory nerve behaviour. The model used by STAR allows various non-linear properties to be implemented such as neural response adaptation and threshold adaptation. Also, the stimulus times of STAR are based on threshold crossing times rather than at times of local maxima as specified for the Travelling Wave Sound Processor.

The TESM strategy contains an element similar to the neural adaptation effect that is part of the present invention. However, the increasing of amplitude of short-duration amplitude transitions in the TESM strategy is based on a direct estimate of the slowly varying signal envelope and then rules are applied for applying a gain factor. A consequence of the method used by TESM is that a delay of 30 ms is introduced in the signal. In one embodiment, the present invention applies the adaptation function continuously to the sequence of spikes and does not rely on examination of time periods to estimate gain as TESM does. Thus, not only is the technique different, but no extra time delay is introduced.

The following description refers in more detail to the various features of the method and system for generating electrical stimuli of the present invention. To facilitate an understanding of the invention, reference is made in the description to the accompanying drawings where the invention is illustrated in a preferred embodiment. It is to be understood however, that the invention is not limited to the preferred embodiment as shown in the drawings.

Figure 1:
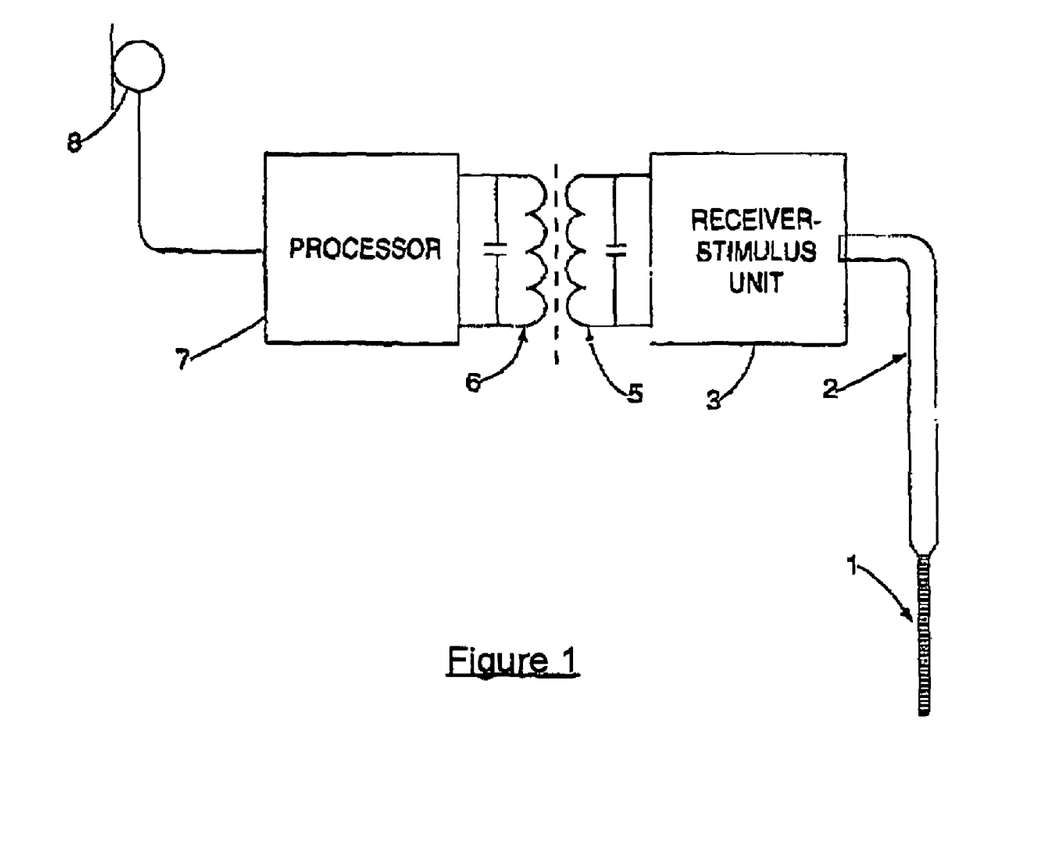
FIG. 1 is a schematic diagram of one embodiment of a system for stimulating an electrode array implanted into a cochlea.

Referring now to FIG. 1, there is shown generally a system for stimulating an electrode array in accordance with a processed signal. An electrode array 1, implanted into a cochlea, connects via cable 2 to a receiver-stimulator unit (RSU) 3. The implanted system receives control signals and power from an external speech processor unit, preferably via a tuned coil RF system 5, 6 as illustrated. However, any alternative connection technique such as percutaneous connection may be employed.

The coil 6 carries a signal modulated by the processor 7 so as to cause the RSU 3 to stimulate the electrodes in the electrode array in the desired sequence, timing and amplitude. The processor 7 in turn receives electrical analog signals from a microphone 8 worn by the user. The present invention is concerned with the operation of the processor and particularly the method of processing the incoming electrical signal.

Figure 2:
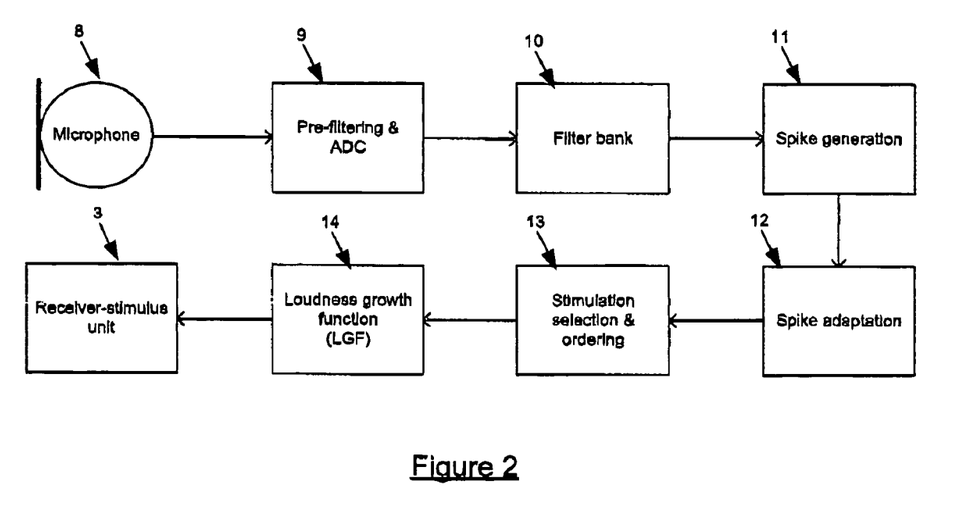
FIG. 2 is a schematic diagram showing the function blocks of a processor forming part of the electrode stimulation system of FIG. 1.

FIG. 2 illustrates the various functional blocks of the processor 7, including a pre-filtering & ADC block 9, a filter bank 10, a spike generation block 11, a spike adaptation block 12, a stimulation selection & ordering block 13 and a loudness growth function block 14. The pre-filtering & ADC block 9 may be implemented using known electronic circuitry and analog signal sampling techniques, whilst the functional blocks 10 to 14 may be implemented using known digital signal processing techniques.

Pre-filtering and Analog-to-Digital Conversion

Sound is recorded by the microphone 8, which may inherently apply pre-emphasis to the incoming signal. This signal is low-pass filtered, to prevent aliasing during sampling, and is then sampled by an analog-to-digital converter in the pre-filtering and ADC block 9. In an embodiment of the invention using the CI-24M cochlear implant, the signal is sampled by the analog-to-digital converter at 14.4 kHz.

Filter Bank

The digitally sampled audio signal is passed through the filter bank 10 spanning the region of approximately 200-7200 Hz. The number of filters will depend on the cochlear implant device used and the number of electrodes available for a particular implant user, which is typically 22 channels in the Cochlear Ltd Nucleus™ electrode array but varies across devices. The centre-frequencies (CFs) of the filters are distributed using a psychophysical pitch scale, such as mel-scale or bark scale, in a similar way to standard frequency distributions for electrodes in commonly used cochlear implant frequency-electrode maps. The filter bandwidth is proportional to the equivalent rectangular bandwidth obtained from the psychophysical critical band measurements. The filter bank is designed along the lines of that designed by Kim et al. (1999, op cit) for automatic speech recognition, except that the number of filters is different and IIR filters may be used instead of FIR filters.

Spike Generation

Figure 3:
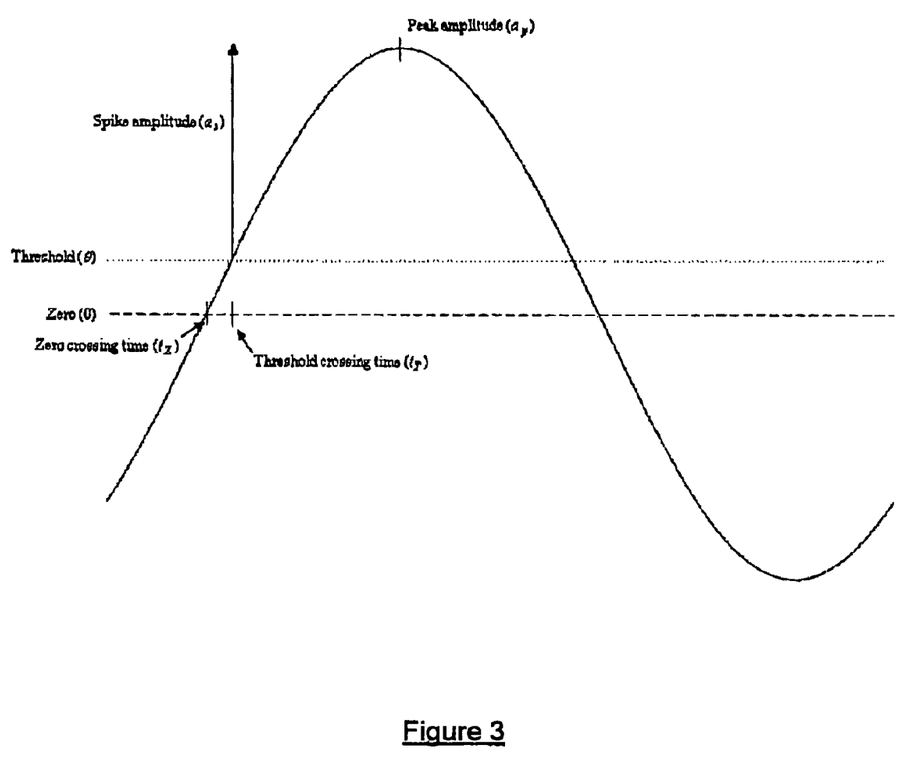
FIG. 3 is an exemplary filtered representation of an audio signal received by the electrode stimulation system of FIG. 1.

Spikes are generated in the spike generation block 11 from the filtered signal representation in a manner similar to that used by Kim et al. (1999, op cit) except that threshold-crossing times rather than zero-crossing times are used. This allows adaptation of the strategy to ambient long-term noise levels. As can be seen in FIG. 3, a spike is generated at time $t_T$ of a positive-going crossing of the threshold. An amplitude is assigned to the spike by subtracting the peak amplitude from the threshold. The peak amplitude is found by searching ahead in the channel for the maximum amplitude of the filtered signal representation before a following negative-going threshold crossing. The search is limited to 10 ms, or 1440 samples, to prevent significant processing time lag in the strategy.

Figure 4:
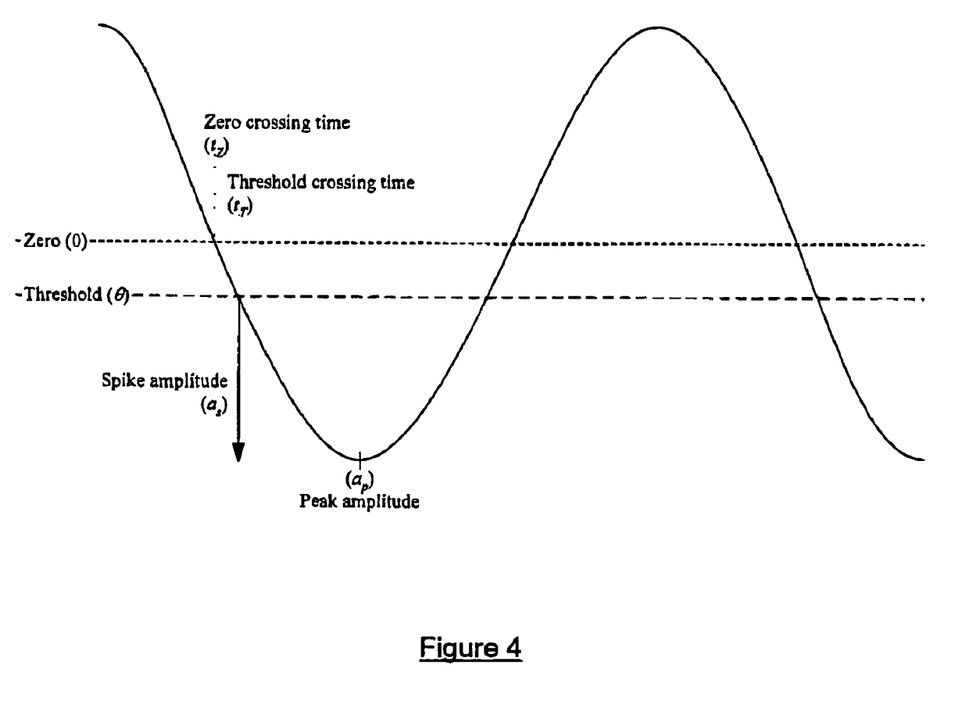
FIG. 4 is second exemplary filtered representation of an audio signal received by the electrode stimulation system of FIG. 1.

FIG. 4 depicts an alternative embodiment in which the spike time is time $t_T$ is determined by the negative-going crossing of the threshold. The amplitude is assigned to the spike by subtracting the peak amplitude from the threshold in a fashion analogous to that of the embodiment of FIG. 3. The peak amplitude is found by searching ahead in the channel for the maximum amplitude in the negative direction of the filtered signal representation before a following positive-going threshold crossing. Again, as for the FIG. 3 embodiment, the search is limited to 10 ms, or 1440 samples, to prevent significant processing time lag in the strategy.

The spike time, or temporal position of a spike, is the sample time closest to the threshold-crossing time plus the number of sample periods corresponding to the travelling-wave delay associated with the distance along the electrode array of the electrode corresponding to the particular filter. If this delay time is $\alpha(n)$, where n is the filter number, then the spike time is $t_s = t_T + \alpha(n)$. Accordingly, the temporal position of each spike is delayed by a travelling wave delay that would exist for a normally hearing person along the length of the electrode array, $$\alpha(n) = C_D e^{C_L x(n)},$$

where $C_D$ is the travelling wave delay coefficient, $C_L$ is the length coefficient for the travelling wave delay and x(n) is the propagation distance for electrode n. Typical values for $C_D$ and $C_L$ may be obtained from measurements reported in the literature. For example, for one person described in Donaldson, G S and Ruth, R A (1993, Derived band auditory brainstem response estimates of travelling wave velocity in humans. I: Normal-hearing subjects, J. Acoust. Soc. Am.93 (2):940-951) the coefficients are $C_D$=0.3631 and $C_L$=0.11324, and x(n) is distance from the stapes in mm. In the preferred implementation, x(n) is the distance of electrode n from the most basal electrode that is in use. In another implementation of the invention, x(n) is computed by determining the effective distance of electrode n from the round window based on the location in the normal cochlea of the centre frequency of the filter for that electrode using a frequency-place map function.

In the embodiment of FIG. 3, each spike has a temporal position based upon an instant at which the filtered signal representation crosses the threshold $\theta$ in a positive direction. The amplitude of each spike is derived from the amplitude $\alpha p$ of the filtered signal representation peak following the threshold crossing. In this case, spike amplitude is equal to the difference between the threshold $\theta$ and the amplitude $\alpha_p$. However, spike amplitude may alternatively be equal to the amplitude $\alpha_p$ itself.

In other embodiments though, the threshold may be the zero axis and each spike may have a temporal position based upon an instant at which the filtered signal representation crosses the zero axis (referenced 0 in FIG. 3) in a positive direction. The amplitude of each spike may be derived from the amplitude $\alpha_p$ of a filtered signal representation peak following the zero axis crossing. Spike amplitude may be equal to the difference between the threshold $\theta$ and the amplitude $\alpha_p$. Alternatively, spike amplitude may be equal to the amplitude $\alpha_p$ itself.

In the embodiment of FIG. 4, each spike has a temporal position based upon an instant at which the filtered signal representation crosses the threshold in a negative direction. The amplitude of each spike is derived from the amplitude of the filtered signal representation peak following the threshold crossing. In this case, spike amplitude is equal to the difference between the threshold and the amplitude. However, spike amplitude may alternatively be equal to the amplitude itself.

As discussed in relation to the embodiment of FIG. 3, the threshold may be the zero axis and each spike may have a temporal position based upon an instant at which the filtered signal representation crosses the zero axis. (referenced 0 in FIG. 4) in the negative direction.

Spike Adaptation

Adaptation effects modelled on neural adaptation are applied to each generated spike by the spike adaptation block 12 based on the previous history of the spike train in each channel. The adaptation is controlled by a variable obtained by integrating over all previous spikes with an appropriate decay function. A gain derived from the adaptation variable is applied to the spike amplitude $t(\alpha_s)$ to obtain an adapted version $(\alpha_s^A)$ that may be greater than the original amplitude when the integral is small. With sustained activity, the integral will increase thus making $(\alpha_s^A)$ reduce back to $\alpha_s$. The equation for this complete operation is $$\alpha_S^A = \alpha_s + \frac{L_A}{C_s^A} \alpha_s (1 - \Gamma_A), \Gamma_A = \gamma_A = \gamma_A \sum_{t_z, < t_s} \alpha_s, e^{-(t_s - t_{s'})/\tau_A},$$

where $C_A$ is the maximum value permissible for an adapted spike, $C_S$ is the maximum sustained amplitude permissible for a spike sequence, $\gamma_A$ is a normalising term to control rate of adaptation, $\tau_A$ is a time constant controlling rate of decay of previous spike train influence on the current spike, $t_s$ is the time of the current spike, $t_{s'}$ represents the times of the previous spikes and $a_s$ represents the amplitudes of the previous spikes. The summation is implemented in recursive form in the digital signal processor as a single value for each channel that is continually updated with each spike arrival.

The spike adaptation block 12 also acts to adapt the value of the threshold based on the long-term average energy of the filtered signal representation.

In one implementation of this procedure, the threshold, $\theta$, is adjusted by the previous sequence of generated spikes for each filter. An equation of the form $$\theta_s = \theta_{s-1} e^{-(t_s - t_{s-1})/\tau_n} + C_n a_s$$

may be used, where $\theta_s$ is the new threshold computed after the generation of the current spike s at time $t_s$, based on the previous threshold $\theta_{s-1}$ that was computed at the previous spike time $t_{s-1}$. The time constant $\tau_n$ is set for each filter based on the centre frequency of that filter to control the rate of decay of the threshold. The value $a_s$ is the amplitude of the current spike, which was computed using the threshold established for the previous spike, and $C_n$, is a constant for each filter to control the rate of growth of the threshold.

Stimulation Selection and Ordering

There are a number of issues that are important to consider when selecting an electrode stimulation sequence. These are:
1. The maximum pulse rate delivered to a single cochlear implant electrode may be limited to a fixed maximum average rate. This may be usually controlled by limiting the maximum average stimulation rate per electrode, for example, to 2000 pulses per second (pps).
2. The cochlear implant has a maximum possible total rate of stimulation. For example, in the Cochlear CI-24M device, this is 14,400 pps.
3. Stimulation of multiple electrodes should be non-simultaneous to avoid current interactions within the cochlea. Therefore, there should be a means of arbitrating contention between spikes with simultaneous arrival times.
4. Each cochlear implant user has a different mapping between current level on each electrode and perceived loudness. Thus threshold (T) and comfort (C) levels should be established for each user and for each electrode. Overall adjustments of T and C levels may often be made, usually downward, after fitting the map to account for loudness summation across multiple electrodes when the device is actually being used with sound input. A loudness growth function (LGF) should be applied to transform spike height to current level.

The creation of a stimulation sequence by the stimulation selection & ordering block 13 commences in each cycle by establishing a stimulation selection window of duration where is the number of stimulation intervals permitted within the bound of the maximum average stimulation rate. For a 2000 Hz maximum average rate of stimulation per electrode, the minimum time between successive stimuli on a single electrode should be, on average, greater than or equal to 0.5 ms. A maximum total stimulation rate for an implant of 14,400 Hz provides about 0.07 ms per stimulus. In this example, stimulation intervals. An integer value of can be used to select a longer window for a cycle of electrode sequence selection and also the limit on the number of times each electrode may be stimulated within that window such that the maximum stimulation rate is not exceeded. In the preferred implementation of the invention. It will be appreciated that in other embodiments of the invention higher maximum total stimulation rates and higher maximum average stimulation rates may be used.

The spikes from each channel that occur with the window are then considered for selection as electrode stimuli. The spikes may be combined across channels and are ordered by normalised amplitude. The normalisation is determined from configuration of the entire prosthesis, particularly the characteristics of the microphone 8 and the filter bank 10, as well as the properties of speech, so that the priority of spikes in different frequency regions can be incorporated into the sorting procedure.

After sorting, the list of sorted normalised amplitude spikes is progressively examined to obtain a stimulation sequence for the window. The top candidate is selected (i.e. the candidate with the largest normalised amplitude) and a stimulation pulse is placed in a stimulation time slot corresponding to the closest time to the spike time. The process continues until all time slots within have been filled. If a stimulation pulse is to be placed in a slot that is already filled, then neighbouring slots are examined in the following order: [−1+1−2+2−3+3 . . . ] where −1 indicates the previous slot, +1 is the next slot, −2 is the slot before the previous one, etc. Only slots within window may be examined in this way.

Loudness Growth Function

After each cycle of electrode selection, the stimuli are mapped to current levels using the standard loudness growth function (LGF) and the stored map (T and C levels) for the user by the loudness growth function block 14. The LGF is a logarithmic function relating stimulus level to loudness to obtain an appropriate increase in subjective loudness. The stored map specifies the minimum and maximum current levels permitted for a user. A special C level may be specified for short duration transient events to allow increased levels during an adaptation step.

IMPLANT STIMULATION

The stimulus sequence is then transmitted to the receiver-stimulus unit 3 that interfaces with the cochlear implant and encodes the electrode selection and current level information to the device.

Finally, it is to be understood that various modifications and/or additions may be made to the method and system for generating electrical stimuli described herein without departing from the spirit or ambit of the present invention.

The invention claimed is:

1. A method for processing sound signals to generate electrical stimuli for an auditory prosthesis electrode array including a plurality of electrodes, the method including:

deriving one or more filtered representations of an incoming audio signal;

monitoring the one or more filtered signal representations for a threshold crossing, to detect when the filtered signal representation crosses a predetermined magnitude threshold;

generating a series of spikes from each filtered signal representation to directly control electrode stimulation, and determining for each spike within each of the series of spikes, a different and sequential electrode stimulation time based upon when the corresponding filtered signal representation crossed the predetermined threshold.

2. A method according to claim 1, the method further including:

deriving the amplitude of each spike from the amplitude of a filtered signal representation peak following the threshold crossing.

3. A method according to claim 2, wherein spike amplitude is equal to the difference between the predetermined threshold and the amplitude of a filtered signal representation peak following the threshold crossing.

4. A method according to claim 2, wherein spike amplitude is equal to the amplitude of a filtered signal representation peak following the threshold crossing.

5. A method according to claim 1, wherein the predetermined threshold is the zero axis.

6. A method according to claim 5, the method further including:

deriving the amplitude of each spike from the amplitude of a filtered signal representation peak following the zero axis crossing.

7. A method according to claim 6, wherein spike amplitude is equal to the difference between a predetermined threshold and the amplitude of a filtered signal representation peak following the zero axis crossing.

8. A method according to claim 6, wherein spike amplitude is equal to the amplitude of a filtered signal representation peak following the zero axis crossing.

9. A method according claim 1, the method further including:

delaying the temporal position of each spike according to a travelling wave delay for a normally hearing person along the length of the electrode array.

10. A method according to claim 9, wherein the delay is based on the distance of each electrode relative to the most basal electrode.

11. A method according to claim 9, wherein the delay is based on the effective distance along the basilar membrane of the centre frequency of the filter for each electrode.

12. A method according to claim 1, the method further including:

adapting the threshold based on long-term average energy of the filtered signal representation.

13. A method according to claim 1, the method further including:

computing a neural adaptation variable from an integral of previous spikes in the spike series and from a decay function; and applying a gain derived from the neural adaptation variable to the amplitude of each spike.

14. A method according claim 1, the method further including:

limiting the number of spikes used to generate the electrical stimuli for each electrode so that the number of times a particular electrode is stimulated within a stimulation sequence window does not exceed a fixed maximum average rate.

15. A method according to claim 1, the method further including:
  sorting spikes occurring within a stimulation sequence window in order of importance; and
  selecting a number of the sorted spikes in order of importance to derive an electrode stimulation sequence for generating electrical stimuli.

16. A method according to claim 15, wherein spike importance is determined by normalised amplitude.

17. A method according to claim 15, the method further including:
  configuring normalisation coefficients for comparison and prioritisation of spikes in different frequency regions.

18. A method according to any one of claim 15, the method including:
  encoding the electrode stimulation sequence; and
  transmitting the encoded electrode stimulation sequence to the auditory prosthesis electrode array to enable stimulation of an auditory nerve or cochlear nucleus.

19. A method according to claim 15, the method including:
  obtaining the electrode stimulation sequence by progressively placing spikes occurring within the stimulation sequence window in decreasing order of importance from a sorted list of normalised amplitude spikes in stimulation time slots corresponding to the temporal positions of the spikes.

20. A method according to claim 1, the method further including:
  mapping electrical stimuli to a current level for a particular user using a loudness growth function and stored threshold and comfort levels for that particular user, wherein the mapping uses a special comfort level for short duration transient events to provide increased stimulation levels during neural response adaptation.

21. A method as claimed in claim 1 wherein each spike in the series of spikes has a temporal position based upon an instant at which the filtered signal representation crosses a predetermined threshold in a positive direction.

22. A method as claimed in claim 1 wherein each spike in the series of spikes has a temporal position based upon an instant at which the filtered signal representation crosses a predetermined threshold in a negative direction.

23. A system for stimulating an auditory prosthesis electrode array, including:
  a stimulator unit for selectively stimulating electrodes in the electrode array; and
  a processor for processing received sound signals and controlling the operation of the stimulator unit to generate electrical stimuli for an auditory prosthesis electrode array including a plurality of electrodes, said processor being configured to:
  derive one or more filtered representations of an incoming audio signal;
  monitor the one or more filtered signal representations for a threshold crossing to detect when the filtered signal representation crosses a predetermined magnitude threshold;
  generate a series of spikes from each filtered signal representation to directly control electrode stimulation and to determine for each spike within each of the series of spikes, a different and sequential electrode stimulation time based upon when the corresponding filtered signal representation crossed the predetermined threshold.

24. The system of claim 23 wherein the processor is further configured to:
  derive the amplitude of each spike from the amplitude of a filtered signal representation peak following the threshold crossing.

25. The system of claim 23 wherein spike amplitude is equal to the difference between the predetermined threshold and the amplitude of a filtered signal representation peak following the threshold crossing.

26. The system of claim 23 wherein spike amplitude is equal to the amplitude of a filtered signal representation peak following the threshold crossing.

27. The system of claim 26 wherein the predetermined threshold is the zero axis.

28. The system of claim 27 wherein spike amplitude is equal to the difference between a predetermined threshold and the amplitude of a filtered signal representation peak following the zero axis crossing.

29. The system of claim 23 wherein the processor is further configured to:
  delay the temporal position of each spike according to a travelling wave delay for a normally hearing person along the length of the electrode array.

30. The system of claim 29 wherein the delay is based on the distance of each electrode relative to the most basal electrode.

31. The system of claim 23 wherein the delay is based on the effective distance along the basilar membrane of the centre frequency of the filter for each electrode.

32. The system of claim 23 wherein the processor is further configured to:
  adapt the threshold based on long-term average energy of the filtered signal representation.

33. The system of claim 23 wherein the processor is further configured to:
  compute a neural adaptation variable from an integral of previous spikes in the spike series and from a decay function; and
  apply a gain derived from the neural adaptation variable to the amplitude of each spike.

34. The system of claim 23 wherein number of spikes used to generate the electrical stimuli for each electrode is limited so that the number of times a particular electrode is stimulated within a stimulation sequence window does not exceed a fixed maximum average rate.

35. The system of claim 23 wherein the processor is further configured to:
  sort spikes occurring within a stimulation sequence window in order of importance; and
  select a number of the sorted spikes in order of importance to derive an electrode stimulation sequence for generating electrical stimuli.

36. The system of claim 35 wherein the stimulator unit is configured to:
  encode the electrode stimulation sequence; and
  transmit the encoded electrode stimulation sequence to the auditory prosthesis electrode array to enable stimulation of an auditory nerve or cochlear nucleus.

37. The system of claim 23 wherein the processor is further configured to:
  map electrical stimuli to a current level for a particular user using a loudness growth function and stored threshold and comfort levels for that particular user, wherein the mapping uses a special comfort level for short duration transient events to provide increased stimulation levels during neural response adaptation.

38. The system of claim 23 wherein each spike in the series of spikes has a temporal position based upon an instant at which the filtered signal representation crosses a predetermined threshold in a positive direction.

39. The system of claim 23 wherein each spike in the series of spikes has a temporal position based upon an instant at which the filtered signal representation crosses a predetermined threshold in a negative direction.

40. A processor for use in a system for stimulating an auditory prosthesis electrode array, the system including a stimulator unit for selectively stimulating electrodes in the electrode array, the processor including digital signal processing means for processing received sound signals and controlling the operation of the stimulator unit to generate electrical stimuli for an auditory prosthesis electrode array, the processor being further configured to:

derive one or more filtered representations of an incoming audio signal;

monitor the one or more filtered signal representations for a threshold crossing, to detect when the filtered signal representation crosses a predetermined magnitude threshold; and generate a series of spikes from each filtered signal representation to directly control electrode stimulation, and to determine for each spike within each of the series of spikes, a different and sequential electrode stimulation time based upon when the corresponding filtered signal representation crossed the predetermined threshold.

41. The processor of claim 40 wherein the processor is further configured to:

derive the amplitude of each spike from the amplitude of a filtered signal representation peak following the threshold crossing.

42. The processor of claim 41 wherein spike amplitude is equal to the difference between the predetermined threshold and the amplitude of a filtered signal representation peak following the threshold crossing.

43. The processor of claim 41 wherein spike amplitude is equal to the amplitude of a filtered signal representation peak following the threshold crossing.

44. The processor of claim 40 wherein the predetermined threshold is the zero axis.

45. The processor of claim 44 wherein spike amplitude is equal to the difference between a predetermined threshold and the amplitude of a filtered signal representation peak following the zero axis crossing.

46. The processor of claim 40 wherein the processor is further configured to:

delay the temporal position of each spike according to a travelling wave delay for a normally hearing person along the length of the electrode array.

47. The processor of claim 46 wherein the delay is based on the distance of each electrode relative to the most basal electrode.

48. The processor of claim 40 wherein the delay is based on the effective distance along the basilar membrane of the centre frequency of the filter for each electrode.

49. The processor of claim 40 wherein the processor is further configured to:

adapt the threshold based on long-term average energy of the filtered signal representation.

50. The processor of claim 40 wherein the processor is further configured to:

compute a neural adaptation variable from an integral of previous spikes in the spike series and from a decay function; and apply a gain derived from the neural adaptation variable to the amplitude of each spike.

51. The processor of claim 40 wherein number of spikes used to generate the electrical stimuli for each electrode is limited so that the number of times a particular electrode is stimulated within a stimulation sequence window does not exceed a fixed maximum average rate.

52. The processor of claim 40 wherein the processor is further configured to:

sort spikes occurring within a stimulation sequence window in order of importance; and select a number of the sorted spikes in order of importance to derive an electrode stimulation sequence for generating electrical stimuli.

53. The processor of claim 40 wherein the processor is further configured to:

map electrical stimuli to a current level for a particular user using a loudness growth function and stored threshold and comfort levels for that particular user, wherein the mapping uses a special comfort level for short duration transient events to provide increased stimulation levels during neural response adaptation.

54. The processor of claim 40 wherein each spike in the series of spikes has a temporal position based upon an instant at which the filtered signal representation crosses a predetermined threshold in a positive direction.

55. The processor of claim 40 wherein each spike in the series of spikes has a temporal position based upon an instant at which the filtered signal representation crosses a predetermined threshold in a negative direction.

* * * * *